(12) United States Patent
Blick et al.

(10) Patent No.: US 7,939,346 B2
(45) Date of Patent: May 10, 2011

(54) NANOMEMBRANES FOR REMOTE SENSING

(75) Inventors: Robert H. Blick, Madison, WI (US);
Robert David Nowak, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 990 days.

(21) Appl. No.: 11/753,919

(22) Filed: May 25, 2007

(65) Prior Publication Data
US 2008/0293152 A1 Nov. 27, 2008

(51) Int. Cl.
*G01N 33/48* (2006.01)
(52) U.S. Cl. .................. 436/527; 422/68.1
(58) Field of Classification Search ............. 436/527; 422/68.1
See application file for complete search history.

(56) References Cited

U.S. PATENT DOCUMENTS

| | | | |
|---|---|---|---|
| 5,192,507 A * | 3/1993 | Taylor et al. | 422/68.1 |
| 7,211,464 B2 * | 5/2007 | Lieber et al. | 438/99 |

OTHER PUBLICATIONS

Huang, M., et al., "Nanomechanical Architecture of Strained Bilayer Thin Films: From Design Principles to Experimental Fabrication," *Advanced Materials* 17, 2860-2864 (2005).
Qin, H., et al., "Formation of microtubes from strained SiGe/Si heterostructures," *New Journal of Physics* 7, 241 (2005).
Bajwa, W., et al., "Compressive Wireless Sensing," *ISPN'06*, Apr. 19-21, 2006, published by ACM.
Py, Charlotte, "Capillary Origami: Spontaneous Wrapping of a Droplet with an Elastic Sheet," *Physical Review Letters* 98, 156103 (2007).
Waheed Bajwa et al, Source-Channel Communication for Field Estimation in Wireless Sensor Networks, Information Processing in Sensor Networks: Proceedings of the 4th international symposium on Information processing in sensor networks, 2005, Article No. 44, IEEE Press.

* cited by examiner

*Primary Examiner* — Lyle A Alexander
(74) *Attorney, Agent, or Firm* — Bell & Manning, LLC

(57) ABSTRACT

The present invention provides sensors for use in detecting the presence or absence of analytes, systems incorporating the sensors, and methods for using the sensors. The sensors include thin membranes that undergo a detectable geometry change upon exposure to an analyte. In one exemplary embodiment, the sensors are small, thin-film membranes that include a stained semiconductor bilayer, wherein an interaction between the membrane and an analyte induces a detectable change in a strain-induced curvature of the membrane.

17 Claims, 8 Drawing Sheets

NANOMEMBRANES FOR REMOTE SENSING

FIELD OF THE INVENTION

The present invention relates to the field of sensors and sensor arrays. More particularly, the present invention relates to the field of nanoscale membrane sensors and sensor arrays.

BACKGROUND OF THE INVENTION

Sensors for detecting the presence of a given analyte in solution or in air are known. Such sensors may include mechanical-based sensors such as surface acoustical wave (SAW) devices, or non-mechanical-based sensors such as pH meters. These types of sensors require direct contact with a power supply coupled to electronics for detecting a response in the presence of a given analyte. Distributed wireless sensing systems are a potential alternative to these more conventional sensor systems.

Distributed wireless sensing systems or "sensor networks" are an emerging technology that promises unprecedented ability to monitor and manipulate the physical world via a spatially distributed network of small and inexpensive wireless sensor nodes that have the ability to self-organize into a well-connected network. A wide range of applications of sensor networks have been envisioned. While a practically unlimited range of applications of sensor networks may be imagined, current understanding of their design and management is far from complete.

The vision of massively distributed, autonomous, and untethered sensing systems to monitor spatial phenomena in complex, natural environments captures the grand scope and potential of sensor networks. However, one of the impediments to constructing large-scale distributed sensing systems is the network-centric focus of most research in the distributed wireless sensing arena. It has proven to be incredibly complicated to engineer self-configuring wireless networks, especially in applications where operating conditions are far from ideal. To date, wireless sensor networks involving on the order of 1000 nodes have been deployed with modest success. The vision of tens of thousands, millions, or billions of networked wireless sensors is far from being realized, and it may never materialize. Thus, the network-centric perspective, which is natural and appealing at first, may be a severe limiting factor in the development of large-scale autonomous distributed sensing systems.

SUMMARY OF THE INVENTION

The present invention provides sensors made from nanoscale membranes for use in detecting the presence or absence of analytes, systems incorporating the sensors, and methods for using the sensors to detect the presence or absence of analytes. The sensors, which are thin films having a front surface and a back surface disposed opposite the front surface, undergo a detectable geometry change upon exposure to an analyte resulting from the differential surface forces between the front and back membrane surfaces. The geometry change may be a change in a radius of curvature of the membrane, such that the presence of an analyte can be detected by detecting a change in a curvature of the membranes before, during and/or after exposure of the membranes to an environment suspected of containing the analyte. Detection may be carried out by exposing the membranes to an electromagnetic input signal and detecting a change in an electromagnetic output signal resulting from the exposure of the membranes to an analyte, such that the presence, or even the concentration of, a particular analyte in the environment may be easily detected.

In some instances, the change in membrane geometry may result from a direct interaction between an analyte and the front and/or back surfaces of a membrane. In other instances, the change in membrane geometry may result from an interaction between a binding agent on the front and/or back surface of a membrane and an analyte. In still other instances, the change in membrane geometry may result from a combination of the two types of interactions. Membrane sensitivity to specific analytes can be accomplished by tailoring the membrane surface materials and/or structure or by selecting appropriate binding agents. For example, the binding agents may be bioactive receptors attached to one or more membrane surfaces such that interactions are maximized with respect to an analyte of interest (e.g., a particular protein), while simultaneously minimizing interactions with analytes not of interest.

The sensors are small, thin-film membranes with nanoscale thicknesses, such that many sensors may be scattered over a small surface area. Typically, the membranes will have lateral dimensions (i.e., lengths and widths) of no more than about 100 µm, desirably no more than about 1 µm, and thicknesses of no more than about 500 nm, desirably no more than about 200 nm. For example, one embodiment of the present invention encompasses a sensor comprised of a membrane having a thickness of about 5 to about 200 nm and lateral dimensions of between about 100 nm and 100 µm.

The membranes may be made out of any material that undergoes a detectable geometry change upon exposure to an analyte of interest. Semiconductor materials, and strained semiconductor bilayers in particular, are well-suited for use in the present sensors. The strained semiconductor bilayers include at least two layers of semiconductor materials, wherein one layer is under a strain (e.g., a tensile, elastic or compressive strain) with respect to the other layer due to a lattice mismatch between the two layers. In certain instances the semiconductor bilayer will be elastically strained. The strain in the bilayer creates a curvature along at least part of the membrane. Depending upon the particular system, this strain-induced curvature may be created or enhanced by an interaction with an analyte, or may be eliminated or reduced by an interaction with an analyte. In some embodiments the membranes include a heterostructure with an embedded electron gas which makes it possible to steer the membranes using an electric field. Other advantageous heterostructures are magnetic heterostructures and optically active heterostructures.

Another aspect of the present invention provides methods for using a sensor array comprising a plurality of the membranes to detect the presence or absence of one or more analytes. The methods include the step of dispersing (e.g., scattering) a plurality of membranes in an environment to be tested for the presence of an analyte of interest. Detection of the analyte is accomplished by directing an input signal from an electromagnetic energy source at the plurality of dispersed membranes and measuring a change in the electromagnetic response (i.e., the output signal). Using a sensor array in this manner can have the advantage of providing a plurality of membranes from which an average output signal may be detected, without having to probe all membranes in the array individually.

When the above-mentioned functions are integrated together, the present invention can be understood to comprise a system for detecting the presence of an analyte, the system comprising a sensor array of a plurality of membranes, an electromagnetic energy source for directing an incident electromagnetic signal onto the membranes, and detector for measuring an output signal reflected and/or transmitted by the membranes.

Other principal features and advantages of the invention will become apparent to those skilled in the art upon review of the following drawings, the detailed description, and the appended claims.

BRIEF DESCRIPTION OF THE DRAWINGS

FIG. 3(a) shows a substantially flat nanomembrane.

DETAILED DESCRIPTION OF THE PREFERRED EMBODIMENTS

The present invention provides sensors for use in detecting the presence or absence of analytes, systems incorporating the sensors, and methods for using the sensors. The sensors undergo a geometry change upon exposure to an analyte, which may be detected remotely by monitoring the change in an electromagnetic output signal reflected from the sensors. In one exemplary embodiment, the sensors are small, thin-film membranes that include a strained semiconductor bilayer, wherein an interaction between the membrane and an analyte induces a detectable change in a strain-induced curvature of the membrane. The strained semiconductor bilayers are useful for membranes of the present invention because the membrane geometry, such as radius of curvature, is sensitive to the chemical environment surrounding the membranes. By using the thin membranes of the present invention, surface interactions such as the binding of a ligand to a receptor can be detected by sensing geometry changes in the membrane resulting from the interaction. For example, by using membranes that are both thin and have lateral dimensions reduced to about 100 nm×100 nm, binding to a membrane on the order of only about $10^4$ analyte molecules, or even fewer, can be detected. Membranes of the present invention may be as thin as one atomic layer, or alternatively, membranes having a thickness of up to about 2 microns may be used in the present invention.

The sensors may form the basis of a wireless sensing architecture which allows for remote sensor applications, whereby a plurality of spatially distributed membranes form an array of wireless sensor nodes that have the ability to self-organize into a wireless sensor array that may be monitored remotely. These arrays are well suited for a variety of sensor applications including, but not limited to, geographical monitoring (e.g., disaster relief, environmental monitoring, precision agriculture), machine monitoring (e.g., in a factory or submarine), battlefield sensing and homeland security (e.g., tracking and classifying moving targets) and medicine (e.g., patient monitoring and drug delivery).

Figure 1:
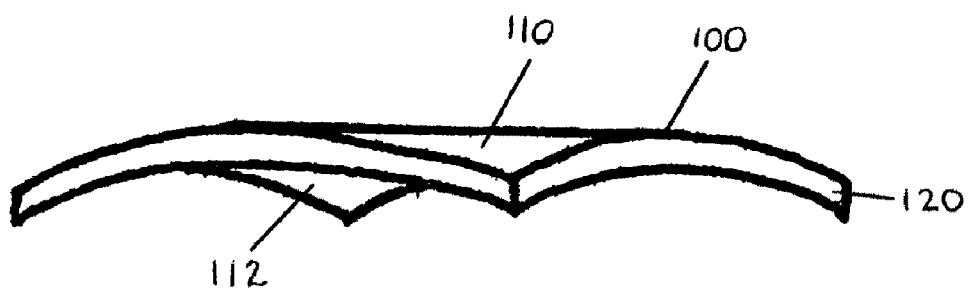
FIG. 1(a) shows a membrane in a substantially flat state.
FIG. 1(b) shows a membrane is a substantially cylindrical state.
Figure 1B:
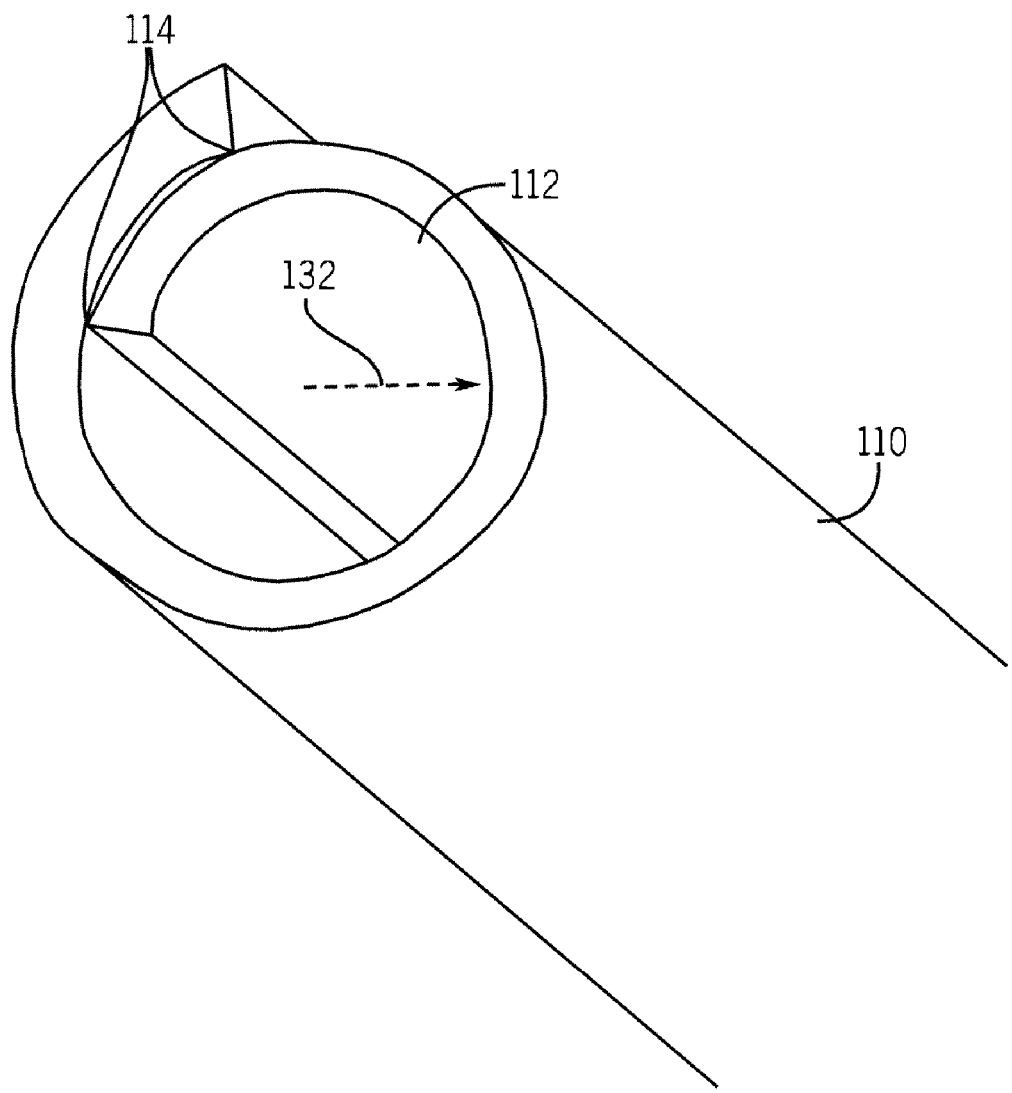

Referring to FIG. 1(a), the membranes 100 of the present invention are characterized by a front surface 110 on one side of the membrane, a second surface 112 disposed opposite the first surface on the other side of the membrane, and a thickness 120. The membrane may be substantially planar as shown in FIG. 1(a), may be substantially curved in one or more directions, a non-limiting example of which is shown in FIG. 1(b), or may have a curvature somewhere in between. Curved membranes may comprise substantially spherical surfaces, in which case each membrane surface may be characterized by a single radius of curvature. Alternatively, the membrane may comprise a torroidal surface, in which case each membrane surface may be characterized by two or more radii of curvature. For example, a cylinder has a radius of curvature in one direction equal to the radius of the cylinder, and an infinite radius of curvature in the longitudinal direction since the surface has no curvature in that direction. For membranes that have more than one radius of curvature, i.e., membranes with non-spherical surfaces, the smallest radius of curvature shall be referred to here as the primary radius of curvature of the membrane, unless otherwise specified.

Referring to FIG. 1(b), the membrane may be curled substantially in one direction, yielding an approximately cylindrical shape with a primary radius of curvature 132 along the cylindrical axis. (As used herein, the term cylindrical shape refers to tubes, coils, helices and similar shapes.) For membranes with large dimensions and/or small radii of curvature, the membrane may curl such that the surfaces 110 and 112 contact each other in one or more locations, creating a contact area 114. Contact area 114 may extend substantially the length of the cylinder, or may only extend for part of the cylinder length, depending on the direction and extent of curling relative to the geometry of the membrane.

Figure 2A:
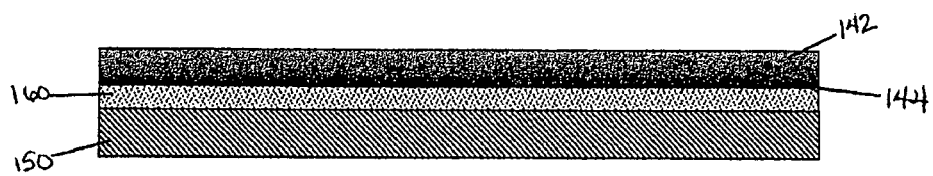
FIG. 2(a) shows an unreleased membrane with two layers on top of a sacrificial layer and substrate.

The membranes of the present invention may comprise one or more layers. Referring to FIG. 2(a), the membranes may for example comprise two layers, 142 and 144, wherein layer 142 is substantially comprised of a first material and layer 144 is substantially comprised of a second material. The compositional change may occur gradually between two or more layers, as depicted by layers 142 and 144 in FIG. 2(a), or the layers may be delineated by a relatively sharp compositional change, as depicted by layers 146 and 148 in FIG. 2(b). A given layer may also itself exhibit a composition gradient of one or more components, which might result from the diffusion of a dopant into a crystalline Si layer, for example.

Figure 3B:
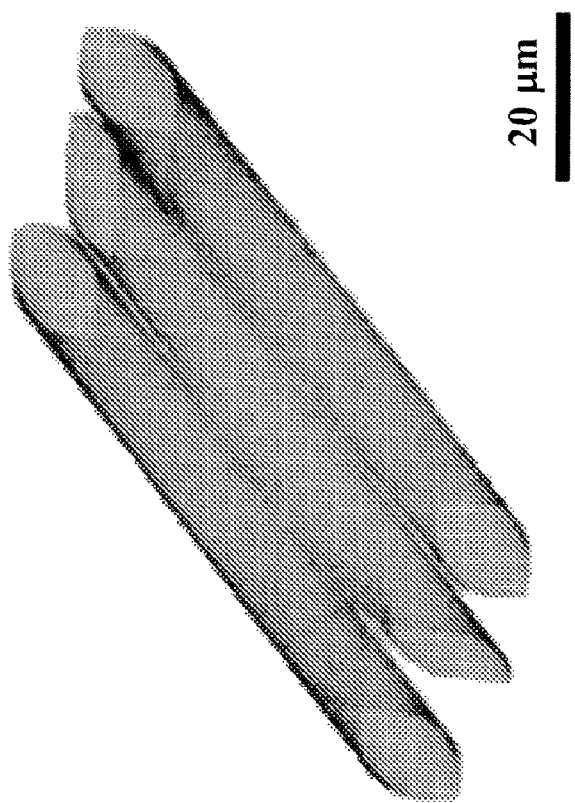
FIG. 3(b) shows nanomembranes rolled into tubes.
Figure 3A:
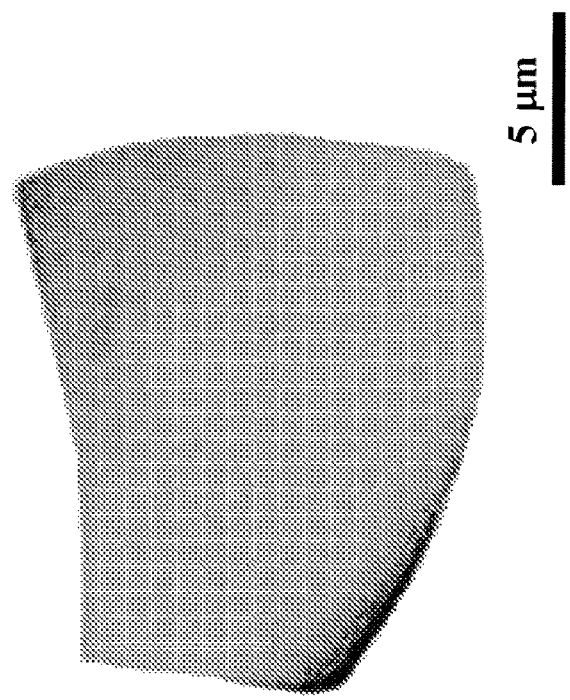
FIGS. 3(a) and (b) show images of nanomembranes made from a SiGe bilayer.

Semiconductor-based membranes may be fabricated using techniques known in the semiconductor processing industry. Using processes from the semiconductor industry to fabricate the membranes of the present invention allows the mass production of substantially identical membranes. Thus, when a given environment is to be tested for the presence of an analyte of interest, large numbers of membranes can be released or dispersed within the environment. This approach creates an array of membrane sensors which do not necessarily interact with each other, but which are all capable of interacting with the environment in a substantially similar manner. Such a membrane array comprises at least 4 membranes, but can contain a substantially higher number of membranes, as high as $10^6$-$10^{10}$ membranes, for example. Other desirable membrane arrays may comprise from about $10^2$ to $10^6$ membranes, or $10^3$ to $10^5$ membranes. The initial geometry of membranes made from strained semiconductor bilayers can be controlled by the strained semiconductor layer sequence of the heterostructure and the geometry defined on the wafer material. FIGS. 3(a) and (b) show images of nanomembranes made from a SiGe bilayer. FIG. 3(a) shows a substantially flat nanomembrane. FIG. 3(b) shows nanomembranes rolled into tubes. The nanomembrane shown in FIG. 3(a) will produce a different output signal than the nanomembranes shown in FIG. 3(b). Methods for forming membranes from strained semiconductor bilayers, including the membranes depicted in FIGS. 3(a) and (b) are described in Huang et al., Adv. Mater., vol. 17, pp. 2860-2864 (2005) and Qin et al., New Journal of Physics, vol. 7, page 241 (2005) the entire disclosures of which are incorporated herein by reference.

Figure 2B:
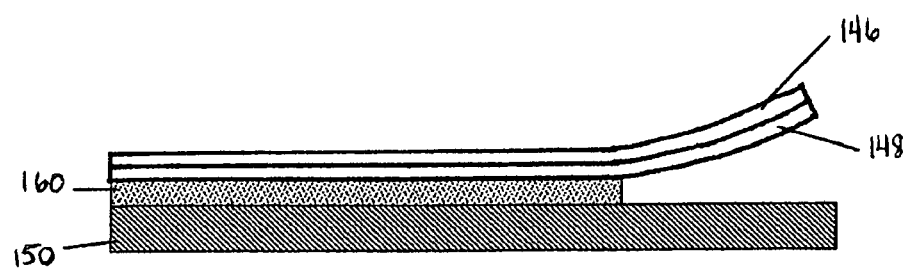
FIG. 2(b) shows a membrane with two layers partially released from a sacrificial layer on a substrate.

By way of illustration, referring to FIG. 2(b), a sacrificial layer 160 is first deposited onto a substrate 150, such as a silicon wafer. The sacrificial layer material should be chosen such that it can be preferentially removed (e.g., etched) relative to the membrane materials. For example, the sacrificial layer may be an oxide, such as silicon dioxide, which may be selectively etched using hydrofluoric acid. Deposition of the sacrificial layer material may also be accomplished by methods well known in the art. Non-limiting examples of such methods include spin-coating for organic-based sacrificial layers, or chemical vapor deposition (CVD) for inorganic-based materials. Where silicon dioxide is to be used as the sacrificial layer, deposition may be accomplished by CVD or plasma-enhanced CVD. Alternatively, a silicon substrate may be oxidized in an oxidizing atmosphere, such as at high temperatures in the presence of oxygen, to create an oxide layer over the substrate.

Next, membrane layer 146 is deposited to a thickness 122 on top of the sacrificial layer. Membrane layer 146 may be a semiconductor material, an insulating material, a conductive material, or a piezoelectric material, for example. Suitable semiconducting materials are well known in the art, and non-limiting examples include Group IV semiconductors such as silicon and germanium, Group III-V compounds such as GaAs, and Group II-VI compounds. Both doped and undoped semiconductors may be employed, including semiconductors with a uniform or non-uniform dopant gradient across the layer thickness 122. The membrane layer 46 may also comprise one or more polymer-based materials. Insulating materials, such as silicon nitride or an organic-based polymer, as well as conductive materials, such as metals, may also be used to form membrane layer 146. Deposition techniques for these materials are well known in the art. Membrane layer 148 may be deposited on top of layer 146 at a thickness 124. Layer 148 may be selected from the same types of materials as disclosed for membrane layer 146, and layer 148 need only differ in composition and/or crystal structure from layer 146. The two layers may differ in dopant concentration or concentration profile, for example. The composition of layer 148 may also be chosen so as to have greater or fewer interactions with an analyte of interest, as compared with layer 146.

The thicknesses of layers 146 and 148 typically range from about 5 nm to about 2000 nm. In certain aspects of the present invention, the thicknesses of layers 146 and 148 will range from about 10 nm to about 1000 nm. In other aspects of the present invention, the thickness of layers 146 and 148 will range from about 50 to about 100 nm. However, other dimensions may be used, provided the membranes remain sufficiently thin to allow for a detectable geometry change in the presence of an analyte.

By way of illustration only, where strained GeSi:Si bilayer membranes are employed, they may be fabricated by starting with well-known SOI (silicon on insulator) or SGOI (silicon-germanium on insulator) wafers or substrates. Such wafers thus already include the substrate 150 (the underlying silicon wafer), the sacrificial layer 160 (the insulator which is typically silicon dioxide), and the first layer of the bilayer 146 (the top silicon layer of an SOI or the SiGe layer of an SGOI). Next, the second layer 148 is grown over the first layer using epitaxy. If SOI is used as the starting material, then an SiGe film may be grown as the second layer. Alternatively, if SGOI is used as the starting material, an Si film may be grown as the second layer. In one aspect, the present invention comprises epitaxial deposition of the second layer having substantially complete registry with the underlying first layer. When the thickness of each layer is kept below the critical thickness at which misfit dislocations occur, the bilayer structures can exhibit elastic strain sharing in which the SiGe layer strains elastically under compressive stress, and the Si layer strains elastically under tensile stress.

Optionally, additional layers may be deposited under, in between, and/or on top of layers 146 and 148. Such additional layers may be chosen in order to improve adhesion between certain materials, to impart conducting or insulating properties to at least one side of the membrane, or to protect the membrane from damage. A layer or a combination of layers may also be chosen to provide reflective or anti-reflective properties as to a given wavelength of electromagnetic radiation.

Once the desired layer or layers are formed, the membrane dimensions are defined by patterning. Well-known patterning techniques from the semiconductor industry may be used to delineate the desired membrane pattern. Non-limiting examples of membrane shapes include circles, squares, and rectangles. Membranes may be patterned into virtually any two-dimensional shape using such techniques as photolithography or electron beam lithography, followed by etching away of the unwanted portions of the membrane layer(s). The lateral membrane dimensions are practically only limited by the substrate size and the patterning techniques used. In certain aspects of the present invention, the largest membrane lateral dimension is no greater than about 2000 microns. In other aspects of the present invention, the largest membrane lateral dimension is no greater than about 100 nanometers. Other desirable membrane lateral dimensions may range from about 1 micron to about 100 microns.

Referring to FIG. 2(b), once the membrane layers 146 and 148 are deposited and patterned into individual membranes, the membranes are released by selective etching of the sacrificial layer 160. Where silicon dioxide is used as the sacrificial layer and the membrane layers comprise crystalline semiconductor films, a suitable etchant is hydrofluoric acid which selectively etches silicon dioxide, thereby releasing the overlying semiconductor layers. Dry etching techniques such as plasma-based etching may also be utilized. As the membrane is released by etching away the underlying sacrificial layer, the membrane may curl upwards or downward in response to a differential stress gradient across the membrane. For example, if layer 146 comprises a SiGe film in compressive stress relative to a Si layer 148 in tensile stress, the membrane will curl upwards as the membrane is released as shown in FIG. 2(b). The degree of curling, or the radius of curvature of the released membrane, will be determined by the overall dimensions of the released portion of the membrane; the composition, crystal structure; and moduli of the membrane layer materials; the thicknesses of the layers; and any differential surface forces between membrane surface 102 and membrane surface 104.

Figure 4:
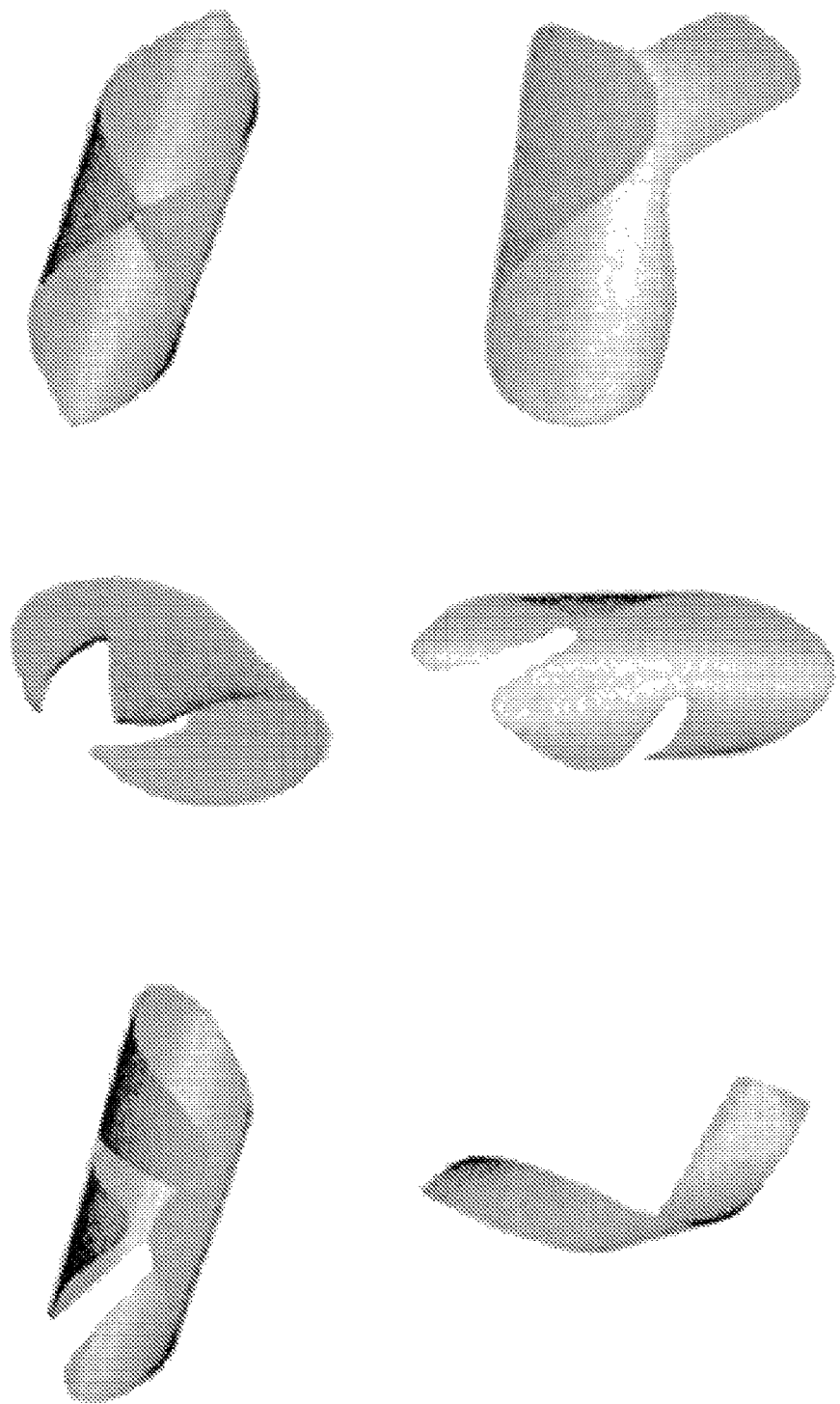
FIG. 4 shows membranes of various geometries fabricated and released from their underlying substrates using concentrated hydrofluoric acid.

In one aspect of the present invention, the membranes may be only partially released from the underlying sacrificial layer and substrate, as depicted in FIG. 2(*b*). In this case the outer portion of the membrane will be free to curl in response to external stimuli, while the center of the membrane remains anchored in place. The degree to which the membrane is undercut and released from the substrate is determined by the time period and the composition of the etchant used to remove the sacrificial layer. Alternatively, the membranes may be completely released from the underlying substrate. Such membranes are then free to float about in solution or to adsorb to or rest upon other surfaces. Fully released membranes may be collected from solution using filtration and/or centrifugation techniques, for example. Membranes of various geometries fabricated and released from their underlying substrates using concentrated hydrofluoric acid are shown in FIG. 4.

Once fabricated, the membranes may be used to detect a variety of analytes by exposing the membranes to the analytes and monitoring geometry changes induced by interactions between the membranes and the analytes. Direct or indirect interactions between membrane surfaces 102 and 104 and one or more analytes can create differential surface forces, thereby affecting the geometry of the membrane, such as the membrane's the radius of curvature. Thus, in some embodiments, direct contact between an analyte and surface 102 and/or 104 induces a change in the geometry of the membrane. In other embodiments, an interaction between an analyte and a binding agent on surface 102 and/or 104 induces a change in the geometry of the membrane. The geometry change may comprise a change in the membrane's radius of curvature from a substantially flat or uncurled state, such as that shown in FIG. 1(*a*), to a substantially curled state, such as that shown in FIG. 1(*b*). In one aspect of the present invention, the membrane geometry change comprises a fluctuation between two states, one state where the primary radius of curvature of the membrane is greater than one of the lateral dimensions of the membrane, and the other state where the primary radius of curvature of the membrane is less than that lateral dimension. In another aspect of the present invention, the membrane geometry change comprises a fluctuation between two states, one state where the membrane is sufficiently curled such that two opposing surfaces contact one another to form a substantially tubular shape, and the other state where the membrane is sufficiently flat such that the membrane surfaces do not contact one another.

The change in membrane geometry may occur when the membranes are in contact with a liquid, solid or vapor or a combination thereof. Thus, for example, the membrane geometry may change from one state when the membranes are in contact with (e.g., submersed, floating or dispersed) in a first liquid, such as water, to a second state when the same membranes come into contact with a second liquid, such as an alcohol. Similarly, the membrane geometry may change when the membrane is exposed to an atmosphere that contains an analyte that adsorbs or otherwise physically interacts with one or more of the membrane surfaces in a manner that affects the membrane geometry.

Sensitizing membranes to analytes of interest may be accomplished in several ways. First, the membrane layer materials may be selected that have an inherent sensitivity to a given analyte, whereby the membrane's geometry changes when it comes into direct contact with the analyte. Alternatively, a surface of the membrane may be functionalized with one or more binding agents, whereby interactions between those binding agents and one or more analytes may induce geometry change in the membrane. The binding agents may be any agents that interact with (e.g., specifically bind to) an analyte of interest in a manner that induces a detectable geometry change in the membrane.

The binding agents may be chemical or biological entities. For example, if the membranes are to be used as sensors in biological applications, the binding agents may be biological ligands or receptors deposited onto one or more membrane surfaces through physical adsorption or covalent attachment. Methods for functionalizing surfaces by attaching ligands and/or receptors to surfaces are well known in the art. In one aspect of the present invention, one or more membrane surfaces may be functionalized by first derivatizing or activating the surface. As non-limiting examples, silicon surfaces may be derivatized with amine, carbonyl, acylchloride, or epoxide functionalities. Such functionalities may optionally include a spacer chain or linker molecule between the functionality itself and the underlying substrate. Once the membrane surface is derivatized or activated, the binding agents desired for selective analyte detection may be attached to the surface at the activated or derivatized sites. Schemes for attaching binding agents to surfaces are well known in the art and include covalent, coordinate, or ionic bonding.

Surface functionalization can be directed, e.g., to attach to the surface molecules with specific linkers to proteins and sugar components in phospholipid membranes. To do so, one can use plasma enhanced chemical modification of the surface. For example, a gentle and efficient cold-plasma-plus-vapor functionalization process to terminate oxide available (including oxidized Si and silicon-on-insulator) surfaces with epoxide or aldehyde groups for chemical attachment of biomolecules is disclosed in B. J. Larson, J. M. Helgren, S. O. Manolache, A. Y. Lau, M. G. Lagally and F. S. Denes, Cold-plasma Modification of Oxide Surfaces for Covalent Biomolecule Attachmentnt, *Biosensors and Bioelectronics,* 21, 796-801, (2005), which is incorporated herein by reference. A variety of biomolecules (including DNA, antibodies, and proteins) have already been attached to bulk oxidized Si as a precursor to functionalizing membranes. Such functionalization has been accomplished with a micron-scale degree of lateral localization.

Functionalization may be accomplished by attaching the desired molecules to a substrate either electrostatically or covalently. Covalent attachment has the advantage that the attached molecules remain bound to the substrate after exposure to target solutions and multiple wash steps. Surface chemical functionalization processes have been developed to bind biomolecules covalently to a range of substrate materials, including glass [Strother, T. C., Cai, W., Zhao, X. S., Hamers, R. J., Smith, L. M., Synthesis and characterization of DNA-modified silicon (111) surfaces, J. Am. Chem. Soc. 2000, 122 (6), 1205-1209], silicon [Conzone, S. D., Pantano, C. G., Glass slides to DNA microarrays. Materials Today 2004, 7 (3), 20-26], and diamond [Yang, W., Auciello, O., Butler, J. E., Cai, W., Carlisle, J. A., Gerbi, J. E., Gruen, D. M., Knickerbocker, T., Lasseter, T. L., J N Russell, J., Smith, L. M., Hamers, R. J., DNA-modified nanocrystalline diamond thin-films as stable, biologically active substrates. Nature Materials 2002, 1, 253-257], the entire disclosures of which are incorporated herein by reference. Most of these processes rely on the use of wet chemistry, in many cases consuming significant volumes of rare, expensive, and/or environmentally unfriendly chemicals. Wet-chemical treatments may take anywhere from several hours to a day to produce a substrate ready for biomolecule attachment.

In another embodiment, functionalization may be accomplished using a cold plasma. Cold plasmas can greatly reduce the complexity of preparing a chemically functionalized surface. A cold (non-equilibrium, near-room-temperature) plasma is an ionized gas produced by applying an electric field to create a discharge in a vapor. An ionized gas permits the modification of even the most chemically resistant surfaces. Although not wishing to be bound by theory, prior efforts directed to the use of cold plasmas of reactive vapors to create specific functionalities on surfaces has not produced exceptional results, primarily because the mixture of different chemical fragments and charge states found in a plasma formed from reactive vapors can produce a mixture of different chemical terminations on the surface [Denes, F., Young, R. A., Sarmadi, M., Surface functionalization of polymers under cold plasma conditions—a mechanistic approach, Journal of Photopolymer Science and Technology 1997, 10 (1), 91-112.]. Improved results are accomplished in accordance with the present invention by carrying out the entire process in vacuum, but using the cold plasma only to activate the surface and then using a vapor of the reactive species that is to be attached to the surface, as described in Larson, B. J.; Helgren, J. M.; Manolache, S. O.; Lau, A. Y.; Lagally, M. G.; Denes, F. S.; Cold-plasma modification of oxide surfaces for covalent biomolecule attachment. Biosensors, in press 2005, the entire disclosure of which is incorporated herein by reference.

The membranes may also be coated with a biocompatible coating in order to make them compatible with biochemical and medical applications. For example, one or more surfaces of the membranes may be partially or completely coated with a parylene coating.

Figure 5:
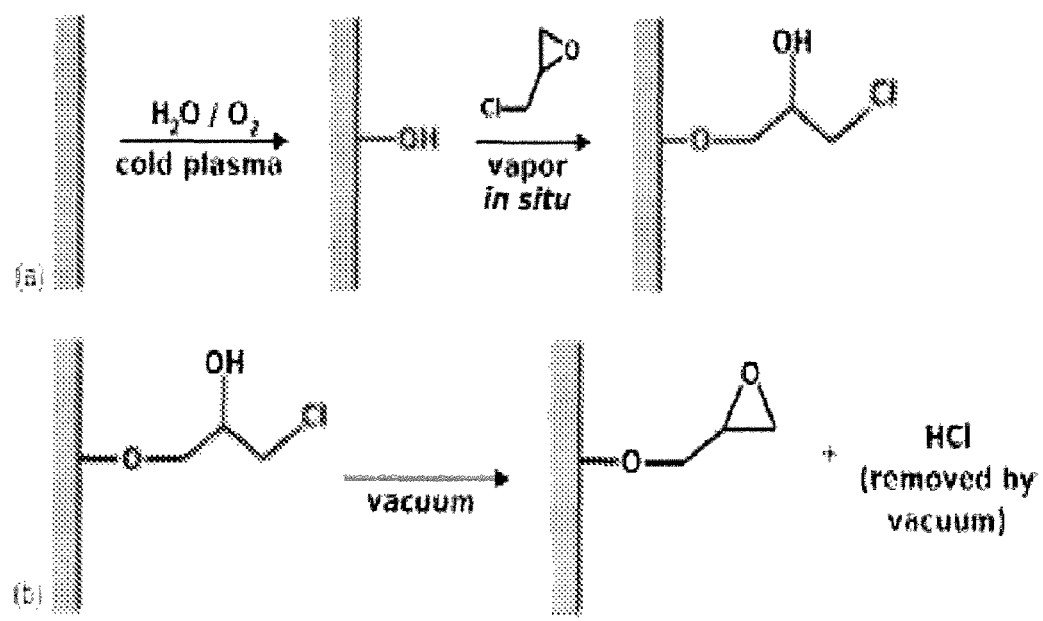
FIG. 5 shows a schematic diagram of a process for the epoxide termination of an oxide surface using a cold-plasma process.

FIG. 5 shows an example of a surface modification treatment sequence using a currently-preferred cold-plasma process wherein an $H_2O/O_2$ cold plasma is used to activate the surface, after which epichlorohydrin vapor is introduced in vacuum to the plasma-activated surface. The reaction of the epichlorohydrin with the surface releases HCl, which is pumped off.

The membrane surfaces may be homogeneously functionalized with binding agents, or they may be functionalized only on certain surfaces or in certain areas of a given surface. As non-limiting examples, the membranes may exhibit functionalization that differs between two opposing surfaces, such as the case where one surface is functionalized and the opposing surface is not. Membrane surface functionalization may also vary across a single surface, by either having areas that are functionalized and areas that are not, or by having more than one type of functionalization across the surface.

One aspect of the present invention provides methods for detecting the presence or absence of an analyte within a given environment by probing the membrane geometry. One technique for probing the membrane geometry is to irradiate the membranes with incident electromagnetic radiation and then to detect the transmitted and/or reflected energy field. Thus, visual observation using radiation in the visible spectrum is one technique whereby the membrane geometry may be probed. Additionally, photoconductivity, dielectric response, polarization and scattering properties can also be measured to detect changes in the membrane geometry. For example, the dielectric response of the membranes can be characterized using mm, sub-mm, and far-infrared wave scattering techniques. For sensors made from strained semiconductor bilayers incident electromagnetic radiation in the frequency range of some 10 GHz over the infrared frequency region into the optical range may be used. Membranes may also be constructed to fluoresce or emit microwave radiation, and the measurement of the emitted signal can be used to detect changes in membrane geometry and thus the presence or absence of an analyte of interest. In certain aspects of the present invention, membranes exhibiting this functionality may comprise III-V or II-VI semiconductor materials The formation of semiconductor layers useful in accordance with the present invention is described more fully in the following disclosures, which are incorporated by reference herein in their entirety: Qin, H.; Shaji, N.; Merrill, N. E.; Kim, H. S.; Toonen, R. C.; Blick, R. H.; Roberts, M. M.; Savage, D. E.; Lagally, M. G.; and Celler; G.; Formation of Micro Tubes from Strained SiGe/Si Heterostructures, *New J. of Physics* 7, 241 2005; Alivisatos, A. P.; Semiconductor Clusters, Nanocrystals, and Quantum Dots, *Science* 1996, 271, 933-937 (1996); Zhang, P. P.; Tevaarwerk, E.; Savage, D. E.; Celler, G.; Park, B. N.; Evans, P. G.; Eriksson, M. A.; Lagally, M. G.; Electronic Transport in Nanometre-Scale Silicon-on-Insulator Membranes, *Nature* 439, 703 (2006); B. J. Larson, J. M. Helgren, S. O. Manolache, A. Y. Lau, M. G. Lagally and F. S. Denes, Cold-plasma Modification of Oxide Surfaces for Covalent Biomolecule Attachmentnt, *Biosensors and Bioelectronics*, 21, 796-801, (2005); Freund, L. B.; Suresh, S., *Thin Film Materials*, ed.; Cambridge University Press: 2003; Prinz, V. Y.; Grutzmacher, D.; Beyer, A.; David, C.; Ketterer, B.; Deckardt, E., A new technique for fabricating three-dimensional micro- and nanostructures of various shapes, *Nanotechnology* 2001, 12, (4), 399-402; Golod, S. V.; Prinz, V. Y.; Mashanov, V. I.; Gutakovsky, A. K., Fabrication of conducting GeSi/Si micro- and nanotubes and helical microcoils, *Semiconductor Science and Technology* 2001, 16, (3), 181-185; Golod, S. V.; Prinz, V. Y.; Wagli, P.; Zhang, L.; Kirfel, O.; Deckhardt, E.; Glaus, F.; David, C.; Grutzmacher, D., Freestanding SiGe/Si/Cr and SiGe/Si/SixNy/Cr microtubes, *Applied Physics Letters* 2004, 84, (17), 3391-3393; Prinz, V. Y.; Seleznev, V. A.; Gutakovsky, A. K.; Chehovskiy, A. V.; Preobrazenskii, V. V.; Putyato, M. A.; Nenasheva, L. A., Free-standing and overgrown InGaAs/GaAs nanotubes: fabrication, potential applications, *In Compound Semiconductors* 1999, ed.; 2000; 78, 199-202; Schmidt, O. G.; Deneke, C.; Schmarje, N.; Muller, C.; Jin-Phillipp, N. Y., Free-standing semiconductor micro- and nano-objects, *Materials Science & Engineering C-Biomimetic and Supramolecular Systems* 2002, 19, (1-2), 393-396; Deneke, C.; Muller, C.; Jin-Phillipp, N. Y.; Schmidt, O. G., Diameter scalability of rolled-up In(Ga)As/GaAs nanotubes, *Semiconductor Science and Technology* 2002, 17, (12), 1278-1281; Schmidt, Q. G.; Eberl, K., Thin solid films roll up into nanotubes, *Nature* 2001, 412, 42-42; Schmidt, O. G.; Jin-Phillipp, N. Y., Free-standing SiGe-based nanopipelines on Si (001) substrates, *Applied Physics Letters* 2001, 78, (21), 3310-3312; Schmidt, O. C.; Schmarje, N.; Deneke, C.; Muller, C.; Jin-Phillipp, N. Y., Three-dimensional nano-objects evolving from a two-dimensional layer technology, *Advanced Materials* 2001, 13, (10), 756-759; Schmidt, O. G.; Deneke C.; M., M. Y., Origami on the micro- and nanometer scale, *Proc. 8th Annu. Int. Conf. Composites Engineering,* 2001, 283; Schmidt, O. G.; Deneke, C.; Kiravittaya, S.; Songmuang, R.; Heidemeyer, H.; Nakamura, Y.; Zapf-Gottwick, R.; Muller, C.; Jin-Phillipp, N. Y., Self-assembled nanoholes, lateral quantum-dot molecules, and rolled-up nanotubes, *IEEE Journal of Selected Topics in Quantum Electronics* 2002, 8, (5), 1025-1034; Schmidt, O. G.; Deneke, C.; Manz, Y. M.; Muller, C., Semiconductor tubes, rods and rings of nanometer and micrometer dimension, *Physica E-Low-Dimensional Systems & Nanostructures* 2002, 13, (2-4), 969-973; Vorob'ev, A.; Vaccaro, P.;

Kubota, K.; Aida, T.; Tokuda, T.; Hayashi, T.; Sakano, Y.; Ohta, J.; Nunoshita, M., SiGe/Si microtubes fabricated on a silicon-on-insulator substrate, *Journal of Physics D-Applied Physics* 2003, 36, (17), L67-L69; Kubota, K.; Fleischmann, T.; Saravanan, S.; Vaccaro, P. O.; Aida, T., Self-assembly of microstage using micro-origami technique on GaAs, *Japanese Journal of Applied Physics Part 1-Regular Papers Short Notes & Review Papers* 2003, 42, (6B), 4079-4083; Kubota, K.; Vaccaro, P. O.; Ohtani, N.; Hirose, Y.; Hosoda, M.; Aida, T., Photoluminescence of GaAs/AlGaAs micro-tubes containing uniaxially strained quantum wells, *Physica E-Low-Dimensional Systems & Nanostructures* 2002, 13, (2-4), 313-316; Ocampo, J. M. Z.; Vaccaro, P. O.; Kubota, K.; Fleischmann, T.; Wang, T. S.; Aida, T.; Ohnishi, T.; Sugimura, A.; Izumoto, R.; Hosoda, M.; Nashima, S., Characterization of GaAs-based micro-origami mirrors by optical actuation, *Microelectronic Engineering* 2004, 73-74, 429-434; Ohtani, N.; Kubota, K.; Vaccaro, P.; Aida, T.; Hosoda, A., Photoluminescence property of uniaxial strained GaAs/AlGaAs quantum wells contained in a micro-tube, *Physica E-Low-Dimensional Systems & Nanostructures* 2003, 17, (1-4), 391-392; Ohtani, N.; Kishimoto, K.; Kubota, K.; Saravanan, S.; Sato, Y.; Nashima, S.; Vaccaro, P.; Aida, T.; Hosoda, M., Uniaxial-strain-induced transition from type-II to type-I band configuration of quantum well microtubes, *Physica E-Low-Dimensional Systems & Nanostructures* 2004, 21, (2-4), 732-736; Hosoda, M.; Kishimoto, Y.; Sato, M.; Nashima, S.; Kubota, K.; Saravanan, S.; Vaccaro, P. O.; Aida, T.; Ohtani, N., Quantum-well microtube constructed from a freestanding thin quantum-well layer, *Applied Physics Letters* 2003, 83, (5), 1017-1019; Legrand, B.; Agache, V.; Nys, J. P.; Senez, V.; Stievenard, D., Formation of silicon islands on a silicon on insulator substrate upon thermal annealing, *Applied Physics Letters* 2000, 76, (22), 3271-3273; Legrand, B.; Agache, V.; Melin, T.; Nys, J. P.; Senez, V.; Stievenard, D., Thermally assisted formation of silicon islands on a silicon-on-insulator substrate, *Journal of Applied Physics* 2002, 91, (1), 106-111; Huang, M.-H., John A. Nairn, M. G. Lagally and Feng Liu, Mechanical Stability of Ultra Thin Ge/Si Film on SiO2: the Effect of Si/Sio2 Interface, submitted to *Applied Physics Letters* 2005; Ejeckam, F. E.; Lo, Y. H.; Subramanian, S.; Hou, H. Q.; Hammons, B. E., Lattice engineered compliant substrate for defect-free heteroepitaxial growth, *Applied Physics Letters* 1997, 70, (13), 1685-1687; Mooney, P. M.; Cohen, G. M.; Chu, J. O.; Murray, C. E., Elastic strain relaxation in free-standing SiGe/Si structures, *Applied Physics Letters* 2004, 84, (7), 1093-1095; Jones, A. M.; Jewell, J. L.; Mabon, J. C.; Reuter, E. E.; Bishop, S. G.; Roh, S. D.; Coleman, J. J., Long-wavelength InGaAs quantum wells grown without strain-induced warping on InGaAs compliant membranes above a GaAs substrate, *Applied Physics Letters* 1999, 74, (7), 1000-1002; Damlencourt, J. F.; Leclercq, J. L.; Gendry, M.; Garrigues, M.; Aberkane, N.; Hollinger, G., Paramorphic growth: A new approach in mismatched heteroepitaxy to prepare fully relaxed materials, *Japanese Journal of Applied Physics Part 2-Letters* 1999, 38, (9AB), L996-L999; Boudaa, M.; Regreny, P.; Leclercq, J. L.; Besland, M. P.; Marty, O.; Hollinger, G., Growth and characterization of totally relaxed InGaAs thick layers on strain-relaxed paramorphic InP substrates, *Journal of Electronic Materials* 2004, 33, (7), 833-839; Tokuda, T.; Sakano, Y.; Mori, D.; Ohta, J.; Nunoshita, M.; Vaccaro, P. O.; Vorob'ev, A.; Kubota, K.; Saito, N., Fabrication and current-drive of SiGe/Si 'Micro-origami' epitaxial MEMS device on SOI substrate, *Electronics Letters* 2004, 40, (21), 1333-1334; Vaccaro, P. O.; Kubota, K.; Aida, T., Strain-driven self-positioning of micromachined structures, Applied Physics Letters 2001, 78, (19), 2852-2854; Vaccaro, P. O.; Kubota, K.; Fleischmann, T.; Saravanan, S.; Aida, T., Valley-fold and mountain-fold in the micro-origami technique, *Microelectronics Journal* 2003, 34, (5-8), 447-449; Liu, F.; Huang, M. H.; Rugheimer, P. P.; Savage, D. E.; Lagally, M. G., Nanostressors and the nanomechanical response of a thin silicon film on an insulator, *Physical Review Letters* 2002, 89, (13); Liu, F.; Rugheimer, P.; Mateeva, E.; Savage, D. E.; Lagally, M. G., Nanomechanics—Response of a strained semiconductor structure, *Nature* 2002, 416, (6880), 498-498; Weig, E. M.; Blick, R. H.; Brandes, T.; Kirschbaum, J.; Wegscheider, W.; Bichler, M.; Kotthaus, J. P., Single-electron-phonon interaction in a suspended quantum dot phonon cavity, *Physical Review Letters* 2004, 92, (4); Yuán, H.-C., Roberts, M. M., Savage, D. E., Ma, Z., and, Lagally, M. G., J., High-Speed Strained-Single-Crystal Silicon Thin-Film Transistors on Flexible Polymers, *Applied Physics Letters*, submitted (2006).

Figure 6A:
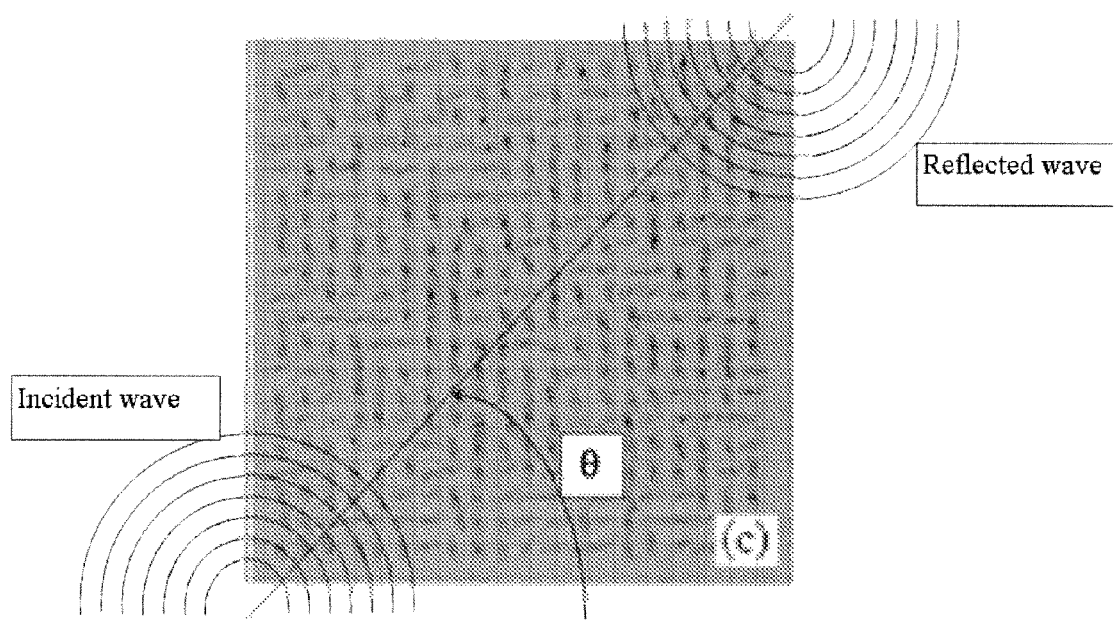
FIG. 6(a) shows an distributed array of membrane sensors on a surface.
Figure 6B:
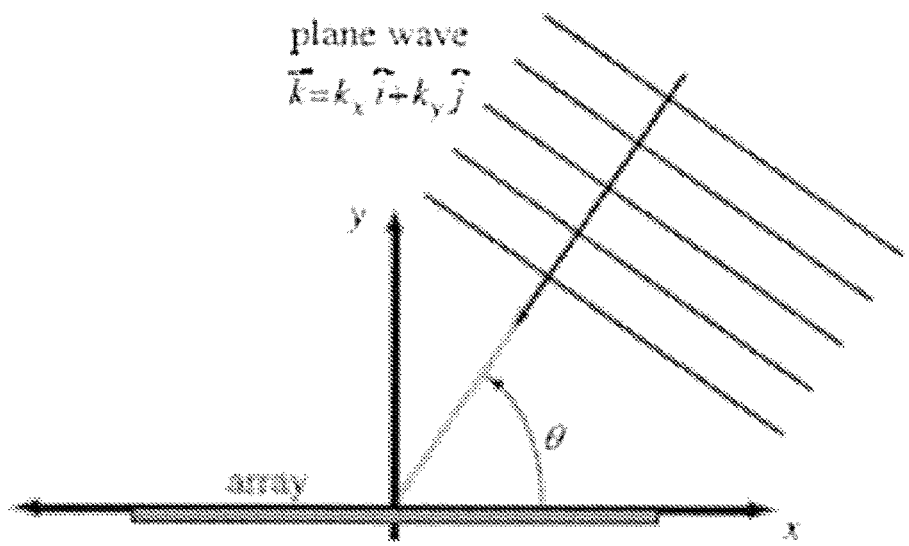
FIG. 6(b) shows a scattering geometry for incident electromagnetic radiation incident on an array of membrane sensors.
Figure 7:
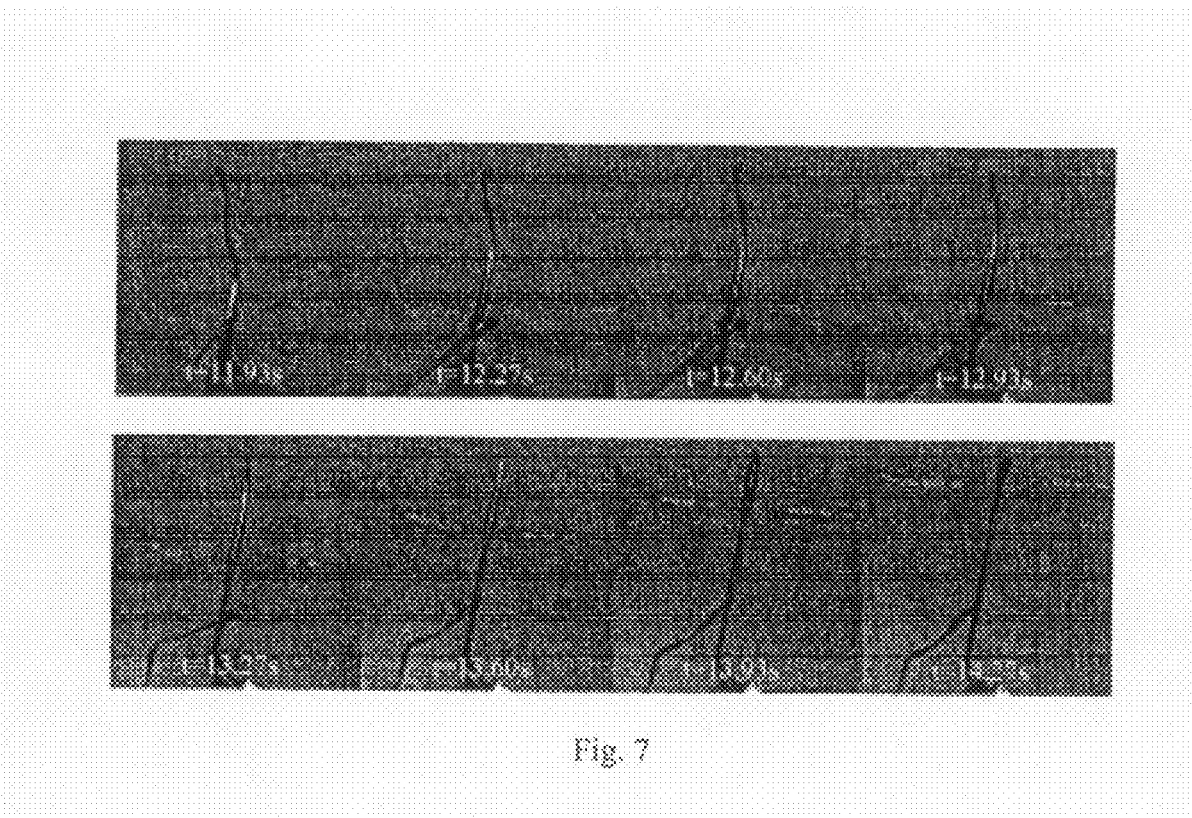
FIG. 7 shows a helical-shaped Si—SiGe strained semiconductor bilayer membrane changing from its curved, helical shape, to its substantially flat shape upon exposure to isopropyl alcohol (IPA).

One embodiment of a membrane array of the present invention is shown in FIG. 6, where FIG. 6(a) depicts a distributed array of substantially cylindrical sensor membranes on a surface and FIG. 6(b) shows a scattering geometry that may be used to measure the electromagnetic response of the sensor array. By way of illustration, in incident beam of electromagnetic radiation may be directed onto an array of sensor membranes and the radiative response of the array may be measured as a function of the frequency of the incident radiation and the incident beam angle to provide a contour plot of the radiative response. Changes in the contour plot (e.g., changes in resonance features in the contour plot) would indicate the presence of an analyte.

Systems that may be adapted to irradiate the membranes with an electromagnetic signal and to measure the transmitted signal are described in Bajwa et al., Compressive Wireless Sensing, in The Fifth International Conference on Information Processing in Sensor Networks, ISPN 2006, pages 134-142; and Bajwa et al., Matched Source-Channel Communications for Field Estimation in Wireless Sensor Networks, in The Fourth International Conference on Information Processing in Sensor Networks, ISPN 2005, pages 332-339, the entire disclosures of which are incorporated herein by reference.

Membrane arrays are useful for sensing the predominant or average change in membrane geometry in a given environment. This eliminates the need to collect information from each individual member of the array, since no single membrane must be specifically located and probed. Rather the electromagnetic source can simply be directed to an area in which the membrane array has been deployed, and any membranes that happen to be within that area will contribute to the collective detected response. The electromagnetic energy source or beam may blanket a relatively large area of the environment to be tested, or may only be incident on a small fraction of the environment. The electromagnetic beam may also be rastered or scanned across the environment to detect membranes within the array.

The present invention further comprises a system for detecting the presence of an analyte, where the system comprises a plurality of membranes, an electromagnetic signal generator adapted to direct an electromagnetic signal onto one or more of the membranes, and a detector adapted to detect an electromagnetic signal reflected from one or more of the membranes. In accordance with this disclosure, the membranes of such a system may comprise semiconductor membranes and/or strained bilayer semiconductor membranes, as described above.

EXAMPLES

Example 1

Membranes comprising a 20 nm layer of Si on top of a 45 nm layer of SiGe were fabricated with lateral dimensions of 8 microns-by-230 microns. The membranes were released from the underlying substrate with concentrated hydrofluoric acid. Dry membranes were curled to form a helix shape and a screen-capture shot of the membranes was taken at t=11.93 s. When an iso-propyl alcohol (IPA) droplet approached the membranes, the membranes uncurled into a substantially flat state, as confirmed in the screen shot taken at t=14.27 s. When the membranes were completely submersed in IPA, they resumed their curled, helical shape. A similar effect was seen using acetone as the analyte.

What is claimed is:

1. A method for detecting the presence of an analyte, the method comprising exposing a plurality of membranes to an environment comprising, or suspected of comprising, the analyte, and detecting a change in the geometry of the membranes caused by an interaction of the analyte with the plurality of membranes, wherein the membranes have a thickness of no greater than about 200 nm and lateral dimensions of no greater than about 2000 microns, wherein the membranes are made from strained semiconductor bilayers comprising at least two layers of semiconductor materials, wherein one layer is under strain with respect to the other layer due to a lattice mismatch between the two layers, and further wherein the change in the geometry of the membrane is a change in a strain-induced curvature of the membrane.

2. The method of claim 1, wherein the membranes have a thickness of no greater than about 100 nm and lateral dimensions of no greater than about 200 microns.

3. The method of claim 1, wherein the membranes have a substantially tubular or helical shape and the measured change in geometry is a change in the average radius of curvature of the substantially tubular membranes.

4. The method of claim 1, wherein the measured change in geometry is a change in a radius of curvature in a first state where the radius of curvature of at least some of the membranes is greater than one of the lateral dimensions of the membranes, and a second state where the radius of curvature of the membranes is less than a lateral dimension of the membranes.

5. The method of claim 1, wherein the strained semiconductor bilayer comprises a SiGe layer and a Si layer.

6. The method of claim 1, wherein the membranes have one or more analyte receptors bound thereto and the change in the geometry of the membranes is caused by the binding of the analyte to the analyte receptors.

7. The method of claim 1, wherein the step of detecting a change in the geometry of the membranes comprises irradiating the membranes with electromagnetic radiation and detecting an electromagnetic response.

8. The method of claim 1, wherein the measured change in geometry is a change in the curvature at one or more edges of the membrane.

9. The method of claim 8, wherein the membranes are anchored to a substrate.

10. The method of claim 1, wherein the environment is a liquid environment.

11. The method of claim 1, wherein the environment is a vapor environment.

12. The method of claim 1, wherein the membranes have a ratio of thickness to length and a ratio of thickness to width in the range from 1:20 to 1:500.

13. A system for detecting the presence of an analyte, the system comprising:
   (a) a plurality of membranes, wherein the membranes have a thickness of no greater than about 200 nm and lateral dimensions of no greater than about 1000 microns and further wherein the membranes have one or more analyte receptors bound thereto, the analyte receptors characterized in that they specifically bind to an analyte, the membranes characterized in that they undergo a change in their radius of curvature when the analytes specifically bind to the analyte receptors, and further wherein the membranes are made from strained semiconductor bilayers comprising at least two layers of semiconductor materials wherein one layer is under strain with respect to the other layer due to a lattice mismatch between the two layers, and further wherein the change in the geometry of the membrane is a change in a strain-induced curvature of the membrane;
   (b) an electromagnetic signal generator adapted to direct an electromagnetic signal onto the plurality of membranes; and
   (c) a detector adapted to detect an electromagnetic signal reflected from the plurality of membranes.

14. The system of claim 13, wherein the membranes have a thickness of no greater than about 100 nm and lateral dimensions of no greater than about 200 microns.

15. The system of claim 13, wherein the membranes are anchored to a substrate.

16. A system for detecting the presence of an analyte, the system comprising:
   (a) a plurality of membranes, wherein the membranes have a thickness of no greater than about 200 nm and lateral dimensions of no greater than about 1000 microns;
   (b) an electromagnetic signal generator adapted to direct an electromagnetic signal onto the plurality of membranes; and
   (c) a detector adapted to detect an electromagnetic signal reflected from the plurality of membranes, wherein the membranes are made from strained semiconductor bilayers comprising at least two layers of semiconductor materials, wherein one layer is under strain with respect to the other layer due to a lattice mismatch between the two layers, and further wherein the change in the geometry of the membrane is a change in a strain-induced curvature of the membrane.

17. The system of claim 16, wherein the strained semiconductor bilayer comprises a SiGe layer and a Si layer.

* * * * *